(12) United States Patent
Garcés et al.

(10) Patent No.: US 6,414,172 B1
(45) Date of Patent: Jul. 2, 2002

(54) HIGH STABLE VEGETABLE OILS

(75) Inventors: Rafael Garcés; Manuel Mancha, both of Seville; José Maria Fernández-Martinez, Cordoba, all of (ES)

(73) Assignee: Consejo Superior de Investigaciones Cientificas, Sevilla (ES)

( * ) Notice: Subject to any disclaimer, the term of this patent is extended or adjusted under 35 U.S.C. 154(b) by 0 days.

(21) Appl. No.: 09/701,870

(22) PCT Filed: May 26, 1999

(86) PCT No.: PCT/EP99/01991

§ 371 (c)(1),
(2), (4) Date: Feb. 27, 2001

(87) PCT Pub. No.: WO99/64546

PCT Pub. Date: Dec. 16, 1999

(30) Foreign Application Priority Data

Jun. 5, 1998 (EP) .............................................. 98201871

(51) Int. Cl.[7] .............................................. C07C 57/00
(52) U.S. Cl. ........................................ 554/227; 800/250
(58) Field of Search ........................... 554/227; 800/200

(56) References Cited

U.S. PATENT DOCUMENTS 5,557,037 A    9/1996  Fehr et al.
5,767,338 A    6/1998  Fan

FOREIGN PATENT DOCUMENTS

| EP | 0 566 216 A3 | 10/1993 |
| EP | 0 797 921 A2 | 10/1997 |
| WO | WO 95/20313 A1 | 8/1995 |

OTHER PUBLICATIONS

Dobarganes, M.C., et al., "Thermal Stability and Frying Performance of Genetically Modified Sunflower Seed (*Helianthus annus* L.) Oils," *J. Agric. Food Chem.* 41:678–681, 1993.

"Storage and Performance Stability of Vegetable Oils," *Food Marketing & Technology* 6(2):20–22, 24, May 1992.

*Primary Examiner*—Deborah D. Carr
(74) *Attorney, Agent, or Firm*—Christensen O'Connor Johnson Kindness PLLC

(57) ABSTRACT

The present invention relates to a vegetable oil which is or can be extracted from seeds and in which at least 12% of the triacylglycerol species that constitute the oil have the general formula SMS and at least 25% of the triacylglycerol species have the general formula SMM, wherein the formula gives from left to right the first, second and third fatty acid in the triacylglycerol and S represents a saturated fatty acid and M represents a monoenoic fatty acid. The invention further relates to a meal obtained as the remainder of the process for extracting the oil from seeds, as well as to the seeds containing the oil and the use thereof for the production of progeny plants having seeds which contain the oil.

37 Claims, 1 Drawing Sheet

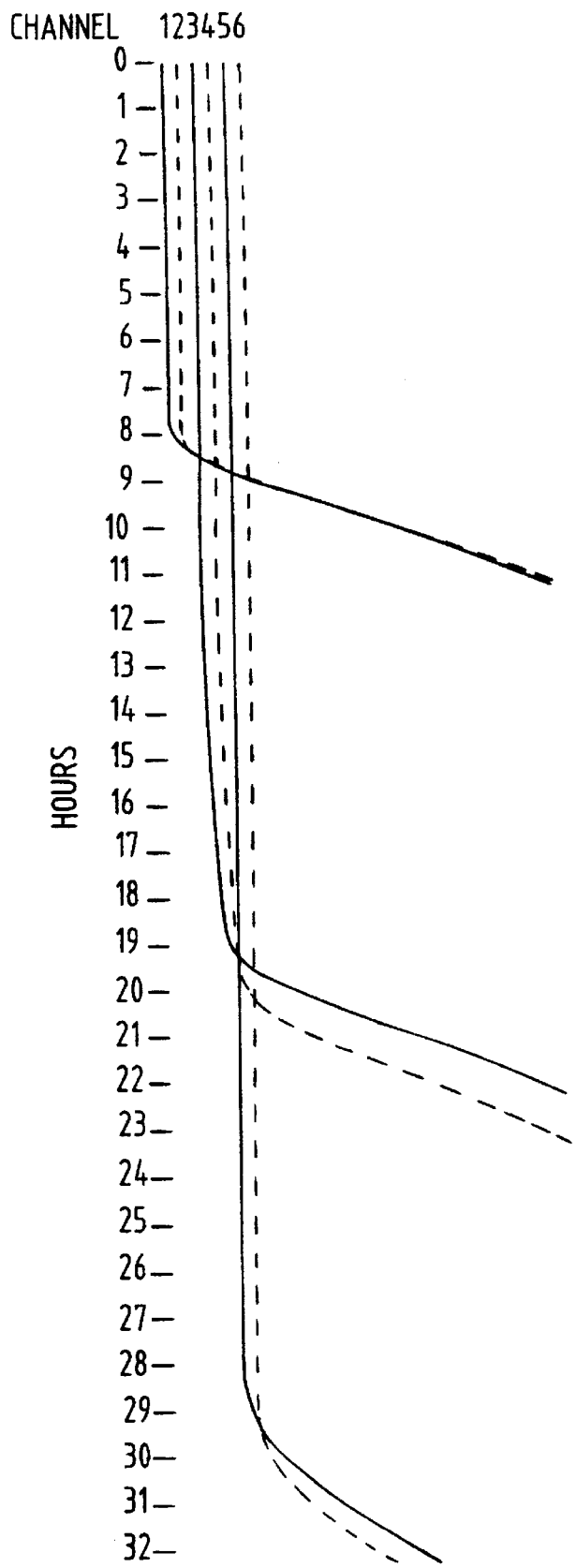

HIGH STABLE VEGETABLE OILS

BACKGROUND OF THE INVENTION

The present invention relates to new vegetable oils, in particular oils from sunflower, soybean, rape, corn etc., which are particularly suitable for applications in which the oil is heated. The invention further relates to the use of the oil, to seeds containing the oil and to by-products of the process of extracting the oil.

Vegetable fats and oils used for deep frying, baking and other applications in the food industry require high thermostability. Partially hydrogenated oils, palm oil and high oleic vegetable oils are commonly used to fulfill this requirement. However, partially hydrogenated fats contain trans isomers of fatty acids that are considered undesirable from a nutritional point of view.

Fats and oils are triesters of glycerol with fatty acids and are called triglycerides or triacylglycerols (herein also identified as "TAG's"). The three fatty acids within a triacylglycerol can be the same or different and may be either saturated or unsaturated. The physical properties of a triacylglycerol depend on its fatty acid composition.

Palm oil and partially hydrogenated fats contain high levels of saturated fatty acids at position sn-2 of their triacylglycerols as compared with most vegetable oils like soybean, sunflower and rape. The location of saturated fatty acids in the sn-2 position has been suggested to be responsible for the atherogenic effects of these acids (Renaud et al., J. Nutr. 125:229–237 (1995)). The use for food applications should therefore be avoided.

BRIEF SUMMARY OF THE INVENTION

In view of the above, there is a need for new natural oils that have higher thermostability and also avoid the excess presence of saturated fatty acids in the sn-2 position of the TAG.

To achieve this the present invention provides a sunflower oil, which is extracted from sunflower seeds and in which at least 12% of the triacylglycerol species that constitute the oil have the general formula SMS and at least 25% of triacylglycerol species have the general formula SMM, wherein the formula gives from left to right the first, second and third fatty acid in the triacylglycerol and S represents a saturated fatty acid and M represents a monoenoic fatty acid. It was surprisingly found that oils of this type have excellent thermostability and also have a lower than 8% of saturated fatty acids content on the sn-2 TAG position.

BRIEF DESCRIPTION OF THE DRAWING

FIG. 1 is a graph showing the thermal stability of high oleic sunflow oil (channels 1 and 2), palm oil (channels 3 and 4), and high palm high oleic (HPHO) oil of the invention (channels 5 and 6), as described in Example 4.

DETAILED DESCRIPTION OF THE INVENTION

The thermostability of the oil of the invention can be expressed as the amount of altered (oxidized TAG monomers and polymerized TAG) triglycerides in oils TAG after a treatment at 180° C. in air during 10 h. For normal sunflower oil (ISLERO®Sunflower, Vanderhave) this value is 24.6%, for high oleic sunflower oil (OLE®, Cargill) it is 21.2% and for an oil according to the invention it was found to vary from 11 to 17%. From this it follows that oil of the invention is significantly more thermostable than the prior art oils.

The triacylglycerol composition of oils of the invention is significantly different from the prior art oils as will be demonstrated in the Examples.

An oil according to the invention can be extracted from seeds of the mutant sunflower line IG-1297M, which seed has been deposited with the American Type Culture Collection (ATCC) on 20 January 1998 under deposit accession number ATCC 209591. The invention is however not limited to the oil extracted from this seed.

The invention resides in the finding that an oil with relatively high amounts of SMS and SMM, preferably at least 12% of SMS and at least 25% of SMM, combines a desirable low amount of saturated fatty acids at position sn-2 and a high thermostability. Such an oil can be obtained from other mutant sunflower lines, for example obtainable by mutagenizing dry seeds with X-rays at 300 cGy/min (beam 200 kV, 18 mA$^{-1}$ and dose 160 Gy). The skilled person will be able to select oils that meet the requirements of the invention by simple testing of the TAG content as described in the Examples.

The oil of the invention is a natural oil that can be extracted from sunflower seeds and used directly without further modification methods to change the TAG content of the invention. Such modification method is for example so-called "hardening" of the oil, which means hydrogenation of double bonds in the fatty acids. The oil of the invention is obtained without performing such artificial modification processes.

A preferred sunflower oil of the invention further comprises at least 8% of triacylglycerol species having the general formula MMM. In addition it is preferred that the oils of the invention have less than 8% saturated fatty acids at position sn-2 of the triacylglycerols that constitute the oil, preferably less than 5%, more preferably less than 3%.

The saturated fatty acids are usually stearic acid and palmitic acid. It is preferred that the oil of the invention has a relatively high palmitic acid content as compared to the stearic acid content, because the oil will then be liquid at room temperature.

To ensure an optimal thermostability it is preferred that the total saturated fatty acid content is at least 25%, more preferably at least 35%, most preferably 45% or more.

It is preferred that the oil in addition has a high oleic acid content, because oleic acid is more stable than linoleic acid and has very good nutritional properties. It is preferred that the oil has in addition less than 15% linoleic acid, more preferably less than 10%, most preferably 5% or lower.

Sunflower oils having a palmitic acid content of at least 23% and an oleic acid content of at least 52% are especially preferred.

In one particular embodiment the sunflower oil of the invention has 20 to 25%, preferably 24.5% triacylglycerols having the general formula SMS, 45 to 55%, preferably 51.9% triacylglycerols having the general formula SMM and 20 to 25%, preferably 22.7% triacylglycerols having the general formula MMM.

The triacylglycerol composition of a sunflower oil that can be extracted from IG-1297M seeds has 21.8% TAG's of the formula POP, 11.1% TAG's of the formula POPo, 1.5% TAG's of the formula PoOPo, 2.7% TAG's of the formula POS, 37.9% TAG's of the formula POO, 9.4% TAG's of the formula PoOO, 2.9k TAG's of the formula SOO, 11.8% TAG's of the formula OOO and 0.9% TAG's of other formulas, wherein P represents palmitic acid, Po represents palmitoleic acid, O represents oleic acid, and S represents stearic acid.

Table 1 shows the minimum and maximum percentages for the various types of TAG's in an oil of the invention.

TABLE 1

|  | Minimum | Maximum |
|---|---|---|
| SSS | — | 1 |
| SMS | 12 | 35 |
| SMM | 25 | 60 |
| SDS | 1 | 10 |
| MMM | 8 | 35 |
| SDM | 1 | 16 |
| MDM | 1 | 13 |
| SDD | — | 2.4 |
| MDD | — | 3.4 |
| DDD | — | — |
| Others | 0 | 1 |

Saturated = S = palmitic and stearic
Monoenoic = M = palmitoleic and oleic
Dienoic = D = linoleic In addition to the oil, the invention relates to sunflower seeds, such as IG-1297M seeds, which seeds contain an oil of the invention. The invention according to another aspect thereof relates to the use of such seeds for extracting sunflower oil therefrom. In addition the invention relates to the use of such seeds for the production of progeny plants having seeds that contain the oil of the invention. The oil of the invention is intended to encompass oil that is already extracted as well as oil that is still present in seeds.

The oil of the invention is thermostable in the sense that it resists oxidation and polymerization of the triacylglycerols that constitute the oil better than known sunflower oils do. As a consequence thereof, the oil of the invention is particularly suitable for frying at temperatures of at least 100° C., preferably 160° C. or 180° C. Frying is intended to encompass frying and stir-frying of food stuffs, such as meat, fowl, fish, fruits, vegetables etc. as well as deep-frying of pastry, fries, snacks. Furthermore, the oil of the invention is also suitable for baking, roasting, cooking etc.

In a more general sense the invention relates to the use of an oil, having less than 15% saturated 10 fatty acids and less than 10%, preferably less than 5% linoleic acid at high temperature conditions. The high temperature conditions are selected from frying and baking. The oil is preferably of vegetable origin, such as sunflower oil.

The invention is not limited to the oil as such. The invention relates also to the use of the oil in mixtures with other oils. In mixtures the overall properties may differ from the oil of the invention.

The oil can be obtained by extracting sunflower seeds containing the oil. In the process of extracting the seeds a meal is formed as a by-product. The invention also relates to this meal. In addition, the invention relates to crushed sunflower seeds, which seeds in their uncrushed state contain a sunflower oil of the invention.

The present invention will be further illustrated in the Examples that follow and that are in no way intended to be limiting to the scope of the invention. Reference is made herein to FIG. 1 showing a comparison of the thermal stability of various oils.

EXAMPLES

Example 1
Preparation of Seeds Containing an Oil of the Invention

The oil of the invention can be obtained from seeds of the deposited strain IG-1297M or from seeds that are obtained in any other way. One other way of obtaining such seed is illustrated hereinbelow.

After X-rays mutagenesis of 5000 dry seeds, 300 cGy/min, beam 200 kV, 18 mA$^{-1}$ and dose 160 Gy with a Siemens Stabilipan (Enlargen, Germany), seeds were grown in spring in the field. Self pollinated plants were collected individually and seeds analyzed for their fatty acid content following the method of Garces and Mancha, Anal. Biochem. 211:139–143 (1993). Seeds with at least three times more saturated fatty acid content than the standard deviation for the specific fatty acid were selected and successively grown until the new character was fixed. Several putative new mutant lines were selected by this method. After further selection for TAG composition line IG-1297M was selected.

Example 2
Extraction of the Oil
1. Plant Material

Mature seeds according to the invention from the line IG-1297M (HPHO) with high palmitic acid content in high oleic background were used. As control materials mature seeds from a normal sunflower line (normal), a high oleic line (HO) (both supplied by Advanta (Marchena, Spain)) and a high palmitic line (HP) (CAS-5, own production) were used.

2. Lipid Extraction

The seeds were ground, mixed with anhydrous sodium sulfate and extracted with petroleum ether in Soxhlet for 5–7 h.

Example 3
Characterization of Triacylglycerols
1. TAG Distribution in the Oil

Purified TAG from Sunflower Seeds of the invention were obtained by passing 3 g oil dissolved in 3 ml petroleum ether over alumina, which had been activated at 200° C. for 3 h immediately before use. The alumina (1.5 g×2) was placed into two small columns connected by a piece of silicone tube and the lipid solution placed on the top and allowed to filter through the alumina. The columns were washed further with 6 ml petroleum ether. The solvent was evaporated and the purified TAG flushed with nitrogen and stored at −20° C.

The TAG were devoid of tocopherols as determined by HPLC following the IUPAC Standard Method 2432 (IUPAC Standard Methods for the Analysis of Oils, Fats and Derivatives, Blackwell, Oxford, 7$^{th}$ ed. (1987)).

The composition of TAG molecular species (Table 2) was carried out by gas chromatography of the purified TAG using a 400–65HT-15–0.1F (Quadrex, Conn., USA) capillary column 15 m×0.25 mm I.D., 0.1 μm film thickness, hydrogen as the carrier gas and FID detector.

Fatty acid methyl esters were obtained by transesterification of the TAG sample with methanol:toluene:SO$_4$H$_2$ (88:10:2 by vol.) at 80° C. for 1 h, according to Garces and Mancha, Anal. Biochem. 211, 139–143 (1993). The fatty acid composition of TAG was carried out by GC of the corresponding methyl esters using an SP-2380 (Supelco, Pa., USA) capillary column, 60 m×0.25 mm I.D., 0.2 μm film thickness, hydrogen as the carrier gas and FID detector.

Table 2A shows that TAG distribution in the oil of the invention (HPHO) is very different from the control oils. Table 2B gives an overall view on the various types of TAG. The amount of SMS and SMM is considerably higher for the HPHO oil of the invention.

TABLE 2A

| | Sunflower oils | | | |
|---|---|---|---|---|
| TAG | Normal | HO | HP | HPHO |
| PPoP | | | 1.4 | |
| POP | | | 3.2 | 21.8 |
| POPo | | | | 11.1 |
| PoOPo | | | | 1.5 |
| PLP | 1.0 | | 27.5 | |
| PLPo | | | 9.1 | |
| POS | | 1.0 | | 2.7 |
| POO | 3.1 | 10.0 | | 37.9 |
| PLS | 1.1 | | 3.7 | |
| PoOO | | | | 9.4 |
| POL | 7.6 | 1.0 | 12.3 | |
| PLL | 6.4 | | 25.2 | |
| PoLL | | | 3.5 | |
| SOO | 2.4 | 10.6 | | 2.9 |
| OOO | 6.8 | 71.7 | | 11.8 |
| SOL | 5.4 | | | |
| OOL | 19.2 | 4.3 | | |
| SLL | 4.9 | | 2.4 | |
| OLL | 26.5 | 1.0 | 4.0 | |
| LLL | 15.1 | | 5.1 | |
| Others | 0.5 | 0.4 | 2.6 | 0.9 |

P = palmitic acid = 16:0
Po = palmitoleic acid = 16:1
S = stearic acid = 18:0
O = oleic acid = 18:1
L = linoleic acid = 18:2

Only TAG with content higher than 1% are shown. The rest are calculated in others.

TABLE 2B

| | Sunflower oils | | | |
|---|---|---|---|---|
| TAG | Normal | HO | HP | HPHO |
| SMS | | 1.0 | 4.6 | 24.5 |
| SMM | 5.5 | 20.6 | | 51.9 |
| SDS | 2.1 | | 31.2 | |
| MMM | 6.8 | 71.7 | | 22.7 |
| SDM | 13 | 1.0 | 21.4 | |
| MDM | 19.2 | 4.3 | | |
| SDD | 11.3 | | 27.6 | |
| MDD | 26.5 | 1.0 | 7.5 | |
| DDD | 15.1 | | 5.1 | |

Saturated = S = palmitic and stearic
Monoenoic = M = palmitoleic and oleic
Dienoic = D = linoleic 2. Thermostability Upon heating the quality of an oil can deteriorate because the TAG's constituting the oil are oxidized and/or polymerized. To test the thermostability a heat treatment at 180° C. during 10 h was performed as follows.

Thermoxidative treatment of the samples was carried out under strictly controlled conditions by making use of a Rancimat (Metrohm Ltd., Herisau, Switzerland) apparatus, according to Barrera-Arellano et al., Grasas Aceites 48, 231–235 (1997)). Briefly, 2±0.01 g of purified TAG were weighed out in standard glass tubes of 13 cm×1 cm I.D., in turn introduced into Rancimat reaction vessels containing 6 g of glycerol to facilitate heat transfer, and inserted in the heating block previously heated at 180±1° C. Samples of 50 mg were withdrawn at 2 h intervals for the analysis of polymerized TAG. After heating for a total period of 10 h, final samples were taken out and additionally analyzed for polar compounds (table 3) and distribution in oxidized TAG monomers and TAG polymers (table 4). Rancimat instructions were carefully observed for cleaning of vessels and temperature correction. No bubbling of air was applied during heating and the vessels were left open.

Polymerized TAG in the various oils were quantified by high-performance size exclusion chromatography (HPSEC) following the IUPAC Standard Method 2508 (supra). Total polar compounds and their distribution in oxidized TAG monomers and TAG polymers were determined by combination of adsorption chromatography and HPSEC (Dobarganes et al. Fat Sci. Tecnol. 90, 308–311 (1988)) (Table 3).

Conditions applied for HPSEC were as follows: A Rheodyne 7725i injector with a 10 μl sample loop and a Waters 510 HPLC pump (Waters Associates, Milford, Mass., USA), two 100 Å and 500 Å Ultrastyragel columns (Waters Associates, Milford, Mass., USA) connected in series and operated at 35° C. and a refractive index detector (Hewlett-Packard, CA, USA) were used. The columns were 25 cm ×0.77 cm I.D., packed with a porous, highly cross-linked styrene divinyl bencene copolymer (<10 Am). HPLC-grade tetrahydrofuran served as the mobile phase with a flow of 1 mL/min. Sample solutions of 50 mg oil/mL and 15 mg polar compounds/ml in tetrahydrofuran were used for the analysis of polymerized TAG and polar compounds distribution, respectively.

TABLE 3

| | Polar compounds | | |
|---|---|---|---|
| Oil | Total oxidized TAG | Oxidized TAG monomers | Oxidized TAG polymers |
| Normal | 24.6 | 9.7 | 14.9 |
| HO | 21.2 | 10.6 | 10.6 |
| HP | 21.1 | 8.9 | 12.2 |
| HPHO | 12.8 | 6.7 | 6.1 |

Table 4 shows the TAG composition of the four different oil types tested. Data are from the original oil (0h) and the composition after 10 hours at 180° C. (10 h). The Oxid. % is the percentage of altered TAG after the 10 hours of the experiment.

TABLE 4

| | Normal | | | HO | | | HP | | | HPHO | | |
|---|---|---|---|---|---|---|---|---|---|---|---|---|
| | 0 h | 10 h | Oxid. % | 0 h | 10 h | Oxid. % | 0 h | 10 h | Oxid. % | 0 h | 10 h | Oxid. % |
| SMS | | | | | | | 4.6 | 4.2 | 8.9 | 25.4 | 22.3 | 12.1 |
| SMM | 5.5 | 5.1 | 7.4 | 20.6 | 16.9 | 18.2 | | | | 51.8 | 45.7 | 11.8 |
| SDS | | | | | | | 31.2 | 27.2 | 12.6 | | | |
| MMM | 6.8 | 6.1 | 9.8 | 71.7 | 56.9 | 20.7 | 21.2 | 18.1 | 14.9 | | | |
| SDM | 12.9 | 10.5 | 18.9 | | | | 12.3 | 10.2 | 17.0 | | | |
| MDM | 19.2 | 14.7 | 23.3 | 4.3 | 2.5 | 42.7 | 9.1 | 7.7 | 15.0 | | | |

TABLE 4-continued

| | Normal | | | HO | | | HP | | | HPHO | | |
|---|---|---|---|---|---|---|---|---|---|---|---|---|
| | 0 h | 10 h | Oxid. % | 0 h | 10 h | Oxid. % | 0 h | 10 h | Oxid. % | 0 h | 10 h | Oxid. % |
| SDD | 11.3 | 8.4 | 25.7 | | | | 27.5 | 19.4 | 29.4 | | | |
| MDD | 26.5 | 18.1 | 31.6 | | | | 7.5 | 5.2 | 30.7 | | | |
| DDD | 15.1 | 9.0 | 40.3 | | | | 5.1 | 2.9 | 43.6 | | | |
| Total | 97.3 | 72.0 | 26.0* | 96.7 | 76.3 | 21.1* | 97.3 | 76.9 | 20.9* | 98.5 | 86.1 | 12.5* |

*Percentage of total oxidized plus polymerized TAG.

Table 5 shows the saturated fatty acids (%) in position sn-2 of the TAG molecules.

TABLE 5

| Oil | Palmitic | Stearic | Total |
|---|---|---|---|
| Normal | 0.8 | 0.6 | 1.4 |
| HO | 0.8 | 0.5 | 1.3 |
| HP | 1.3 | 0.5 | 1.8 |
| HPHO | 1.4 | 0.8 | 2.2 |

Normal = normal sunflower oil
HO = high oleic oil
HP = high palmitic oil
HPHO = high palmitic and high oleic oil = IG-1297M Example 4
Comparison of Thermal Stability The more commonly used method for determining the thermal stability of oils is the Rancimat (developed by Metrohm, Herisau, Switzerland). In this method the results are expressed as hours of oxidation resistance at the indicated temperature. This example compares the two better natural vegetable oils for industrial frying that are currently available in the market, namely high oleic sunflower oil (FIG. 1; channel 1 and 2) and palm olein (FIG. 1; channel 3 and 4), and the HPHO oil of the invention (FIG. 1; channel 5 and 6) at 110° C., conductivity range 200 $\mu$S/cm and delta K 25 $\mu$S/cm. The results show that HPHO is the best. In this experiment the time at delta K=25 $\mu$S/cm of two oil samples of each type was determined (FIG. 1). The mean values were 8.6 h for the HO oil, 19.9 h for the palm olein and 30.4 h for HPHO.

What is claimed is:

1. Vegetable oil extractable from seeds comprising triacylglycerol species in which at least 12% of the triacylglycerol species of the oil have the general formula SMS and at least 25% of triacylglycerol species of the oil have the general formula SMM, wherein S represents a saturated fatty acid and M represents a monoenoic fatty acid.

2. An oil as claimed in claim 1, wherein the seeds are from plants selected from the group consisting of sunflower, soy bean, rape, and corn plants.

3. An oil as claimed in claim 1, further comprising at least 8% of triacylglycerol species having the general formula MMM.

4. An oil as claimed in claim 1, which has less than 8% saturated fatty acids at position sn-2 of the triacylglycerols that constitute the oil.

5. An oil as claimed in claim 4, which has less than 5% saturated fatty acids at position sn-2 of the triacylglycerols that constitute the oil.

6. An oil as claimed in claim 5, which has less than 3% saturated fatty acids at position sn-2 of the triacylglycerols that constitute the oil.

7. An oil as claimed in claim 1, wherein the total saturated fatty acid content is at least 25%.

8. An oil as claimed in claim 7, wherein the total saturated fatty acid content is at least 35%.

9. An oil as claimed in claim 8, wherein the total fatty acid content is at least 45%.

10. An oil as claimed in claim 1 having a palmitic acid content of at least 23% and an oleic acid content of at least 52%.

11. An oil as claimed in claim 1 having 20 to 25% triacylglycerols having the general formula SMS, 45 to 55% triacylglycerols having the general formula SMM and 20 to 25% triacylglycerols having the general formula MMM.

12. An oil as claimed in 11 having 21.8% triacylglycerides of the formula POP, 11.1% triacylglycerides of the formula POPo, 1.5% TAG's of the formula PoOPo, 2.7% TAG's of the formula POS, 37.9% TAG's of the formula POO, 9.4% TAG's of the formula PoOO, 2.9% TAG's of the formula SOO, 11.8% TAG's of the formula OOO and 0.9% TAG's of other formulas, wherein P represents palmitic acid, Po represents palmitoleic acid, O represents oleic acid, and S represents stearic acid.

13. An oil as claimed in claim 1 obtainable by extracting sunflower seeds that have been mutagenized.

14. An oil as claimed in claim 13, wherein the seeds are mutagenized with X-rays at 300 cGy/min, beam 200 kV, 18 mA$^{-1}$ and dose 160 Gy.

15. An oil as claimed in claim 1, which oil is a sunflower oil.

16. An oil as claimed in claim 15 obtainable by extracting sunflower seeds of the mutant sunflower line IG-1297M deposited on Jan. 20, 1998 with the American Type Culture Collection under deposit accession number ATCC 209591.

17. An oil as claimed in claim 1, which is extracted and is for use at high temperature conditions.

18. An oil as claimed in claim 17, wherein the high temperature conditions constitute frying at temperatures of at least 100° C.

19. An oil as claimed in claim 17, wherein the high temperature conditions constitute baking.

20. An oil as claimed in claim 17, wherein the high temperature conditions constitute cooking.

21. An oil as claimed in claim 17, wherein the high temperature conditions constitute roasting.

22. A sunflower oil as claimed in claim 17, wherein the high temperature conditions constitute heating by any means at temperatures of at least 100° C.

23. An oil mixture comprising an oil as claimed in claim 1.

24. A meal obtained as the remainder of a process for extracting oil from seeds, wherein the oil that is extracted is an oil as claimed in claim 1.

25. A meal as claimed in claim 24, which meal originates from sunflower seeds.

26. Crushed seeds, which seeds in their uncrushed state contain a oil as claimed in claim 1.

27. Crushed seeds as claimed in claim 26, which seeds are sunflower seeds.

28. Seeds containing an oil as claimed in claim 1.

29. Seeds as claimed in claim 28, which seeds are sunflower seeds.

30. Sunflower seeds as claimed in claim 29, which seeds are obtainable from a mutant sunflower line.

31. Sunflower seeds as claimed in claim 30, wherein the mutant sunflower line is IG-1297M deposited on Jan. 20, 1998 with the American Type Culture Collection under deposit accession number ATCC 209591.

32. A method of obtaining vegetable oil, comprising crushing seeds as claimed in claim 28, and then extracting the oil therefrom.

33. A method of producing progeny plants having seeds which contain an oil according to claim 1, comprising growing plants from the seeds of claim 28.

34. An oil as claimed in claim 1 having more than 15% saturated fatty acids and less than 10% linoleic acid at high temperature conditions.

35. An oil as claimed in claim 34, wherein the high temperature conditions are selected from frying, baking, roasting, cooking.

36. An oil as claimed in claim 34, wherein the oil is of vegetable origin.

37. An oil as claimed in claim 36, wherein the oil is a sunflower oil.

* * * * *

UNITED STATES PATENT AND TRADEMARK OFFICE
CERTIFICATE OF CORRECTION

PATENT NO. : 6,414,172 B1
DATED : July 2, 2002
INVENTOR(S) : R. Garcés et al.

It is certified that error appears in the above-identified patent and that said Letters Patent is hereby corrected as shown below:

Title page,
Item [75], Inventors, "José Maria Fernández-Martinez," should read -- José María Fernández-Martínez, --

Column 1,
Line 7, "of the." should read -- of the --
Line 62, "(ISLERO®Sunflower," should read -- (ISLERO® Sunflower, --

Column 2,
Line 63, "2.9k" should read -- 2.9% --

Column 3,
Line 41, "saturated 10 fatty" should read -- saturated fatty --

Column 4,
Lines 8 and 57, "Garces" should read -- Garcés --
Line 36, "Sunflower Seeds" should read -- sunflower seeds --

Column 6,
Line 33, "(<10 Am)." should read -- (<10 $\mu$m). --
Line 52, "(Oh)" should read -- (0h) --
Line 62, Table 4, line 8, right justify "21.2  18.1  14.9" into "HPHO" columns Column 8,
Line 32, "formula 000" should read -- formula OOO --

Signed and Sealed this

Eleventh Day of February, 2003

JAMES E. ROGAN
*Director of the United States Patent and Trademark Office*